United States Patent [19]

Pohl

[11] Patent Number: 5,138,887
[45] Date of Patent: Aug. 18, 1992

[54] CLAMPING DEVICE FOR HOLDING A TEST SAMPLE FREE OF ANY BENDING MOMENTS

[75] Inventor: Andreas Pohl, Gross-Umstadt, Fed. Rep. of Germany

[73] Assignee: Carl Schenck AG, Darmstadt, Fed. Rep. of Germany

[21] Appl. No.: 691,447

[22] Filed: Apr. 25, 1991

[30] Foreign Application Priority Data

Dec. 3, 1990 [EP] European Pat. Off. ........ 90123070.6

[51] Int. Cl.⁵ .............................................. G01N 3/02
[52] U.S. Cl. ...................................................... 73/856
[58] Field of Search ............... 73/855, 856, 857, 859, 73/860, 831; 403/57

[56] References Cited

U.S. PATENT DOCUMENTS

| | | | |
|---|---|---|---|
| 213,586 | 3/1879 | Olsen | 73/859 |
| 2,773,368 | 12/1956 | Slaght | 403/57 X |
| 3,347,091 | 10/1967 | Cymmer et al. | 73/103 |
| 4,194,402 | 3/1980 | De Nicola | 73/859 |
| 4,928,532 | 5/1990 | O'Connor et al. | 73/856 |

FOREIGN PATENT DOCUMENTS

| | | |
|---|---|---|
| 3731460 | 4/1988 | Fed. Rep. of Germany . |
| 2196073 | 3/1974 | France . |
| 2626671 | 8/1989 | France . |

*Primary Examiner*—Jerry W. Myracle
*Attorney, Agent, or Firm*—W. G. Fasse

[57] ABSTRACT

A clamping device for holding a sample to be tested in a testing machine is so constructed that an automatic alignment of the clamping device relative to a vertical load application axis is assured to avoid the introduction of undesirable bending moments into the test sample. Thus, tension and/or compression and/or torsion loads can be applied to the test sample without interfering bending moments. For this purpose a clamping shaft is journalled in a support member for journalling about a first axis (9) and the support member is journalled in a mounting buck for journalling about a second axis (13). The mounting buck is secured to the frame of the testing machine. The two journal axes (9, 13) extend perpendicularly to the load application axis (3) of the testing machine. Further, the two journal axes (9, 13) and the load application axis (3) have a common intersection (21).

9 Claims, 4 Drawing Sheets

CLAMPING DEVICE FOR HOLDING A TEST SAMPLE FREE OF ANY BENDING MOMENTS

FIELD OF THE INVENTION

The invention relates to a clamping device or chuck for holding a test sample free of any bending moments, for example, in a testing machine. In such testing machines the test sample may be subjected to tension loads, compression loads, and torsion loads either singly or in combination, but not to bending loads.

BACKGROUND INFORMATION

In the testing of test samples under tension and/or compression loads, it is necessary that the testing load applied in the testing machine is defined as precisely as possible. Thus, when the test sample is clamped in the testing machine it is necessary that bending loads are not applied to the test sample. Such bending loads can result, for example, when the test sample is canted or when the clamping heads are not precisely aligned with each other, for example, due to manufacturing tolerances at the clamping surfaces of the sample or due to similar influences, including thermal expansions and contractions. The application of the testing loads without any bending moments is especially important if the test sample is made of brittle materials such as ceramic materials which require an exactly central force application, since ceramic materials are especially sensitive to bending loads. In order to avoid the application of bending loads to such test samples it is necessary that the testing body is held in such a way in the clamping heads of the testing machine that the load application axis of the testing machine coincides with the longitudinal axis of the test sample. German Patent Publication (DE-OS) 3,731,460 discloses a clamping mechanism which is so adjustable that a test sample is clamped exactly in a centered manner. The known clamping mechanism comprises a clamping plate which holds the test sample and a clamping body which is connected to the loading device. For aligning the test sample, it is possible to adjust or align the clamping plate and the clamping body prior to the beginning of the test, by means of adjustment bolts which permit an adjustment relative to an axial displacement and an adjustment relative to an angular displacement or misalignment. However, during the loading of the test sample, it is possible that the initially aligned sample becomes misaligned relative to the loading axis due to possibly occurring micro-deformations of the test sample or of the clamping head. These length changes of the test sample that occur during the load application to the test sample cannot be compensated in the known apparatus because the clamping plate and the clamping head are adjusted relative to one another prior to the beginning of a testing sequence and because the once adjusted position is rigidly fixed by means of the adjustment bolts.

OBJECTS OF THE INVENTION

In view of the foregoing it is the aim of the invention to achieve the following objects singly or in combination:

to provide a clamping device that permits the clamping of a test sample without the application of bending moments to the test sample due to a continuous automatic self-alignment so that any positional changes of the sample and/or of the clamping elements are compensated automatically and continuously;

to provide a clamping device of the type mentioned above that is simple in its construction, yet will always assure an automatic self-alignment to avoid applying bending moments to the test sample; and to construct the clamping device in such a way that the occurrence of bending moments is positively prevented.

SUMMARY OF THE INVENTION

The clamping device according to the invention is characterized in that a clamping body is rotatably mounted in a support member for journalling about a first axis and that the support member itself is journalled in a force transmitting mounting buck for rotation about a second axis, whereby the first axis extends at right angles to the second axis and so that both rotational axes are extending at right angles to the respective loading axis of the testing machine, whereby the two rotational axes and the loading axis pass through a common intersection. The just mentioned features permit a simple arrangement of components so that the clamping mechanism is easily operable, especially in connection with the testing of very brittle test samples, such as ceramic test samples.

The universal joint type of mounting of the test sample prevents the formation of bending moments in the test sample when the latter is being clamped and also during the subsequent loading of the test sample, because the ends of the test sample can adjust relative to each other substantially free of any loads so that the test sample is always able to align itself in the loading direction. Due to the fact that the universal joint support always assures an automatic adjustment of the testing sample free of bending loads, it is now possible to obviate the measuring of the stress distribution in the probe prior to beginning a testing operation.

According to another suitable embodiment of the invention, the clamping body is constructed as a shaft and the support member is provided with a bore in which the shaft is journalled. This embodiment has the advantage that the manufacturing is simplified and hence can be accomplished in an economic manner. According to a further embodiment, the shaft is provided with a slot extending in the plane of symmetry of the shaft for holding the test sample in a force-locking manner. Thus, it is possible that the clamping end of the test sample is received in the slot and held in place in a force-locking manner by means of clamping screws. Yet another advantageous embodiment provides grooves in the walls forming the slot in the shaft, whereby during the clamping of the test sample ends by means of the clamping screws these grooves, or rather the ridges between the grooves, grip the test sample end like teeth, whereby a force-locking, as well as a form-locking holding of the test sample is achieved.

In still another embodiment of the invention, the clamping body and the support member are mounted in hydrostatic bearings, whereby a low friction mounting is achieved, which is especially free of the so-called Coulomb or static friction.

BRIEF DESCRIPTION OF THE DRAWINGS

In order that the invention may be clearly understood, it will now be described by way of example, with reference to the accompanying drawings, wherein.

DETAILED DESCRIPTION OF PREFERRED EXAMPLE EMBODIMENTS AND OF THE BEST MODE OF THE INVENTION

Figure 1:
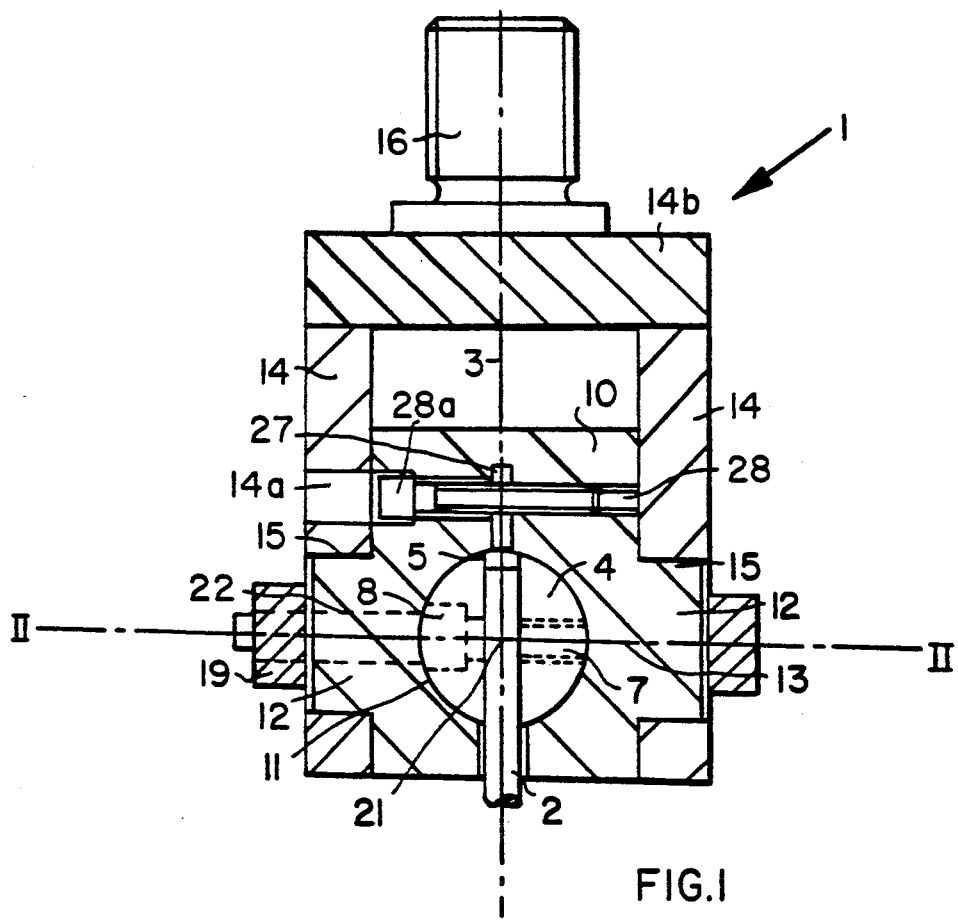
FIG. 1 is a sectional view through a clamping device of the invention for clamping a round test sample with a sleeve bearing for a clamping body.

FIG. 1 shows an upper clamping device 1 constructed for holding a round test sample 2 for applying a tension load and/or a compression load and/or a torsion load to the test sample 2. A second clamping device identical to the device shown in FIG. 1, is holding or clamping the other end of the test sample 2 in a testing machine not shown. The two clamping devices are vertically aligned with their vertical axis, whereby the upper clamping device 1 is, for example, secured to a cross-beam of the loading frame of the testing machine, while the lower clamping device is secured to a loading mechanism, such as a piston cylinder device or the like. The upper and the lower clamping devices are of identical construction, as mentioned, so that it is sufficient to illustrate only the upper clamping device 1. The loading mechanism has a vertical loading axis 3 which, on alignment, coincides with the longitudinal axis of the clamping device 1. The testing loads are applied in the direction of the axis 3. Bending moments are avoided when the load application to the test sample 2 coincides with the loading axis 3. In other words, the loading axis 3 must coincide with the longitudinal axis of the test sample 2 to avoid bending loads.

Figure 2:
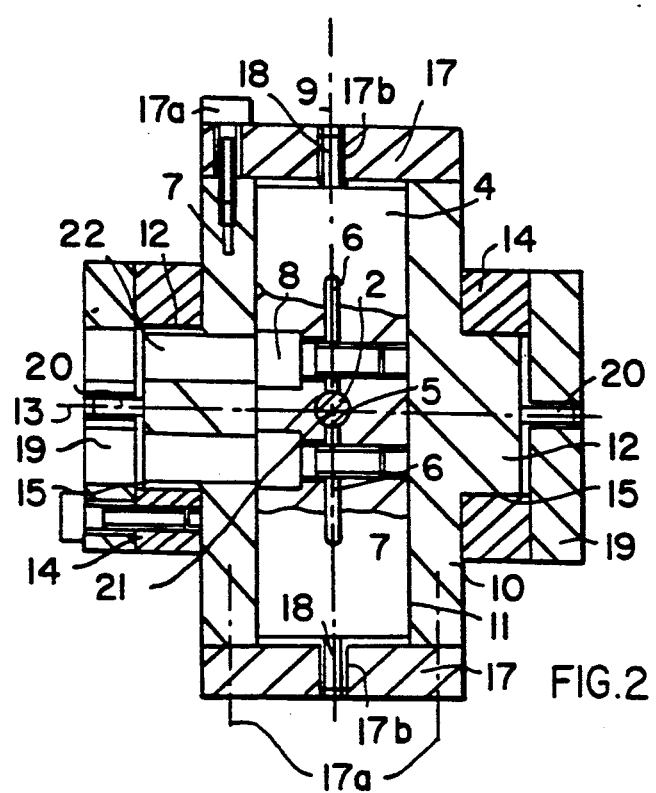
FIG. 2 is a sectional view along section line II—II in FIG. 1.

The end of the test sample 2 is held in a clamping body constructed as a shaft 4. The mounting of the clamping shaft 4 will be described in more detail below with reference to FIG. 2. The clamping shaft 4 has a central through-bore 5 dimensioned to hold the diameter of the end of the test sample 2 which is received in the through-bore 5 that extends vertically through the clamping shaft 4. As shown in FIG. 2, a slot 6 extends through the clamping shaft 4 in the direction of the rotational axis 9 of the clamping shaft 4 on opposite sides of the clamping bore 5. Two threaded through-bores 7 also pass radially through the clamping shaft 4. One threaded bore 7 is arranged on each side of the clamping bore 5. The bores 7 extend perpendicularly to the slots 6 as best seen in FIG. 2. Clamping screws 8 are received in the threaded bores 7. Each clamping screw 8 bridges its respective slot 6 to permit the secure and tight clamping of the end of the test sample 2 in the radial through-bore 5.

The embodiment of FIGS. 1 and 2 can be modified for holding flat test samples rather than round test samples 2. In the modified embodiment the central through-bore 5 is replaced by a slot which extends in the direction of the slots 6 and which has a dimension perpendicularly to the rotational axis 9 of the shaft 4 with due regard to the width of the flat test sample not shown. The clamping is the same as described above for a round test sample. The flat test sample is received in the just described slot and held in place by tightening the screws 8.

When samples made of carbon fiber reinforced composite materials are to be tested, the force-locking clamping of such test samples by clamping screws 8 alone may not be sufficient. It is possible to assure a force-locking clamping even of such test samples by providing grooves and ridges in the walls forming the radial through-bore 5 and the slots 6. When the screws 8 are tightened, the ridges function as clamping teeth which press into the surface of the test sample 2, thereby holding it with a force-locking and a form-locking grip.

As best seen in FIG. 2, the clamping shaft 4 is mounted for rotation in a support member 10, whereby the clamping shaft 4 is journalled about its rotational axis 9. The support member 10 is provided with a through-bore 11 of sufficient diameter to receive the clamping shaft 4 and to permit the rotation of the clamping shaft 4 in the manner of a journal shaft in a slide or sleeve bearing formed by the bore 11 in the support member 10 for the clamping shaft 4 to define second journal bearings.

The support member 10 has two journal pins 12 which are arranged horizontally along a common rotational journal axis 13 extending at a right angle to the rotational axis 9 of the clamping shaft 4. Both journal axes 9 and 13 are located in the same horizontal plane.

The journal pins 12 are rotatable in two bores 15 axially aligned with regard to the journal axis 13 in a mounting or bearing buck 14 having two spaced walls. The spacing between the walls of the bearing buck 14 is such that the support member 10 can be movably received between these walls as best see in FIG. 1. The bores 15 are so dimensioned that a slide bearing is provided for the journal pins 12 to define first journal bearings. Further, the head 28a of a clamping screw 28 passes entirely through a through-bore 14a in a wall of the bearing buck 14 so that the head 28a of the screw will not hinder the journalling movement of the support member 10. The bearing buck 14 comprises a cross-piece 14b to which there is attached a threaded mounting member 16, the longitudinal axis of which coincides with the central vertical load application axis 3. The bearing buck 14 is connected to a cross-beam of the testing machine, not shown, by the threaded mounting member 16. The clamping device at the lower end of the test sample 2 may be secured to the load application device of the testing machine in a similar manner.

The shaft 4 inserted into the support member 10 is held in place against axial displacement in the through-bore 11 by covers 17 held in place by screw bolts 17a. Each cover 17 is provided with a central threaded bore 17b axially aligned with the journal axis 9. A threaded bearing pin 18 is inserted in each threaded bore 17b for permitting a journalling movement of the clamping shaft 4 about the journal axis 9. The threaded bearing pins 18 permit a precise adjustment of the shaft 4 in the axial direction so that the central axis of the radial throughbore 5 in which the test sample 2 is received, can be made to coincide with the loading axis 3.

Instead of mounting the clamping shaft 4 in a slide bearing, the mounting may be accomplished by hydrostatic bearings or by anti-friction bearings, for example, roller bearings so that a low friction mounting is assured, especially when a test load is applied to the test sample, and so that a free journalling of the clamping shaft 4 and of the support member 10 in the bearings is also assured. The clamping shaft 4 and/or the journal pins 12 of the support body 10 and the respective bearing bores 11 and 12 may be coated with a friction reducing layer, for example, of synthetic material, metal carbides, nitrides, or the like, which all have a low friction coefficient. Additionally, or instead, lubricating means may be employed in the mentioned bearings. In this manner the movability or rather the relative movement between the clamping shaft 4 and the journal pins 12 on the one hand, and the surfaces of the bores 11, 15 is increased due to the reduced friction.

The bores 15 in the mounting buck 14 are closed by covers 19 in which also journal centering pins 20 are inserted in respective centered and threaded holes aligned with the journal axis 13.

Adjustment of the threaded centering journal pins 20 permits aligning the center of the support member 10 precisely with the center of clamping shaft 4. The adjustment is performed in such a way that the rotational axis 9 of the clamping shaft 4 and the journal axis 13 of the support 10 extend at right angles to each other and perpendicularly to the loading axis 3 of the testing machine. The adjustment is further made in such a way that the journal axis 9 and 13 and the loading axis 3 have a common intersection 21.

Prior to performing a test operation, a clamping shaft 4 suitable for the particular type of test sample 2, is inserted into the support member 10. As mentioned, the clamping shaft may either have a round through-bore 5 for holding a round test sample, or a flat slot for holding a flat test sample. Thereafter, the test sample 2 is inserted into the radial throughbore 5 and the screws 8 are tightened. For this purpose, the support member 10 and the cover 19 are provided with respective bores 22 which are axially aligned with the threaded bores 7 in which the screws 8 are received. The bores 22 provided in the support member 10 and in the cover 19 make it possible to loosen or tighten the screws 8 even when the clamping shaft 4 is inserted in the support member 10.

The adjustment of the bearing play of the shaft 4 journalled in the bore 11 of the support member 10 is accomplished by a slot 27 that may be tightened or loosened by screws 28. The slot 27 in the support member 10 is axially aligned with the load application axis 3 and extends all the way to the bore 11. The adjustment of the bearing play in the bore 15 of the journal pins 12 in the bearing buck 14 is accomplished by a similar slot not visible in the bearing buck 14, but reaching all the way to the bore 15 and clamped by respective screws.

Figure 3:
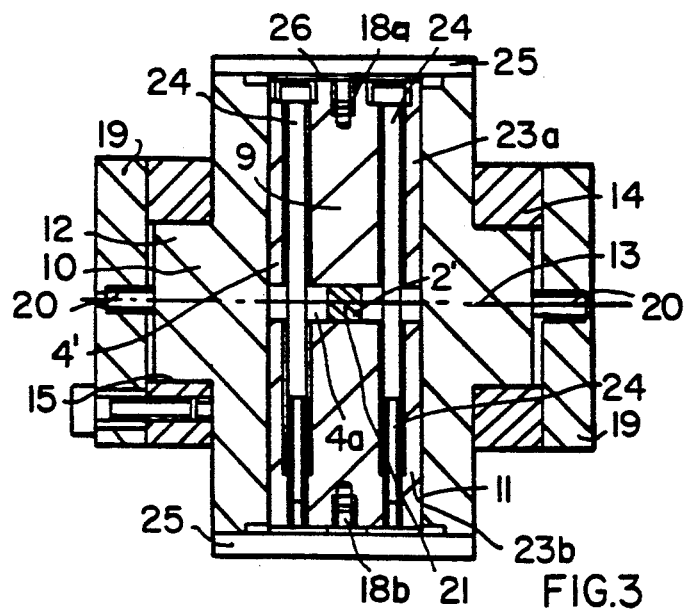
FIG. 3 is a sectional view similar to that of FIG. 2, with jaws for holding a flat test sample.

FIG. 3 illustrates another embodiment of the invention in which the components which are the same as in the first embodiment have the same reference numbers. The test sample 2' in FIG. 3 has a square or flat cross-section. The clamping body 4' is again constructed as a clamping shaft now comprising two shaft sections 23a and 23b separated by a clamping gap 4a in which the test sample 2' is securely held. The clamping gap 4a is centered in a plane that extends perpendicularly to the rotational axis 9. The clamping of the test sample 2' is accomplished by two clamping screws 24 extending in parallel to the journal axis 9 and interconnecting the two clamping shaft sections 23a and 23b. The clamping screws 24 are tight fitting screws with recessed heads as shown in FIG. 3. The shaft 4' is again journalled in a support body 10 for rotation about the journal axis 9. The clamping screws 24 are so-called fit or dowel type bolts. In order to make sure that the tool shaft sections 23a and 23b are symmetrically tightened toward each other and relative to the plane of the journal shaft 13, the ends of the shaft sections 23a, 23b are bearing against closure springs 25 secured at each end to the support body 10 similar to the covers 17 in FIG. 2, however biasing the two shaft sections 23a, 23b inwardly toward each other uniformly, whereby the spring forces are directed axially inwardly centering bearing pins 18a and 18b which are aligned with the journal axis 9 and received in threaded holes of the respective shaft section 23a, 23b, bear against the closure springs 25. Otherwise, the construction of FIG. 3 corresponds to that of FIGS. 1 and 2 as described above.

Figure 4:
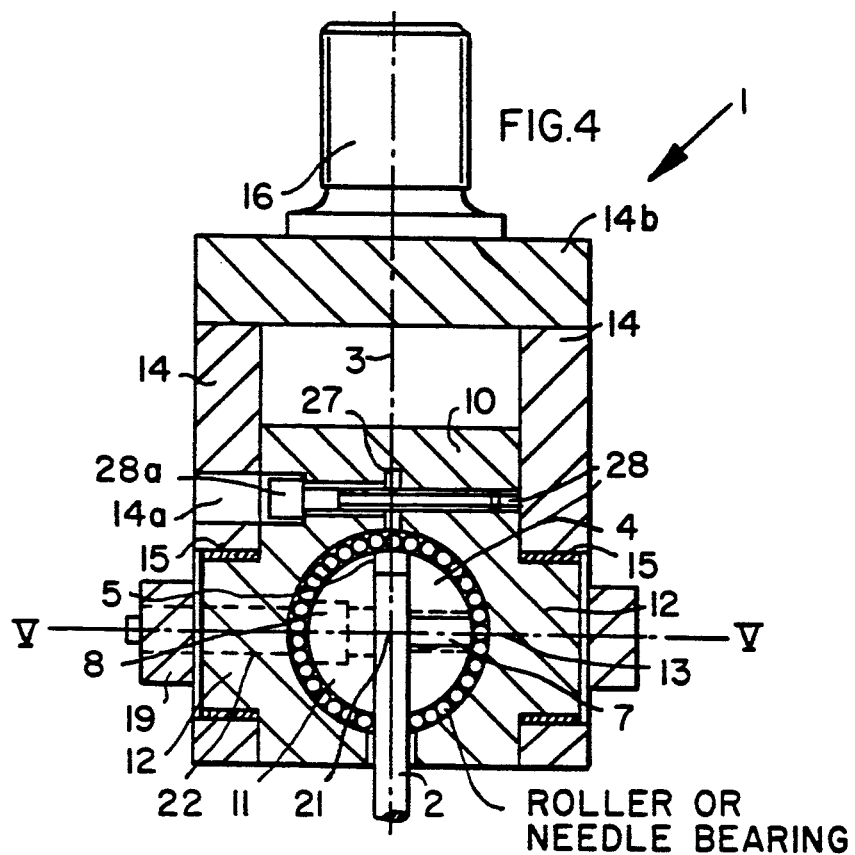
FIGS. 4 and 5 are views similar to FIGS. 1 and 2, but showing a roller or needle bearing for the clamping shaft.
Figure 5:
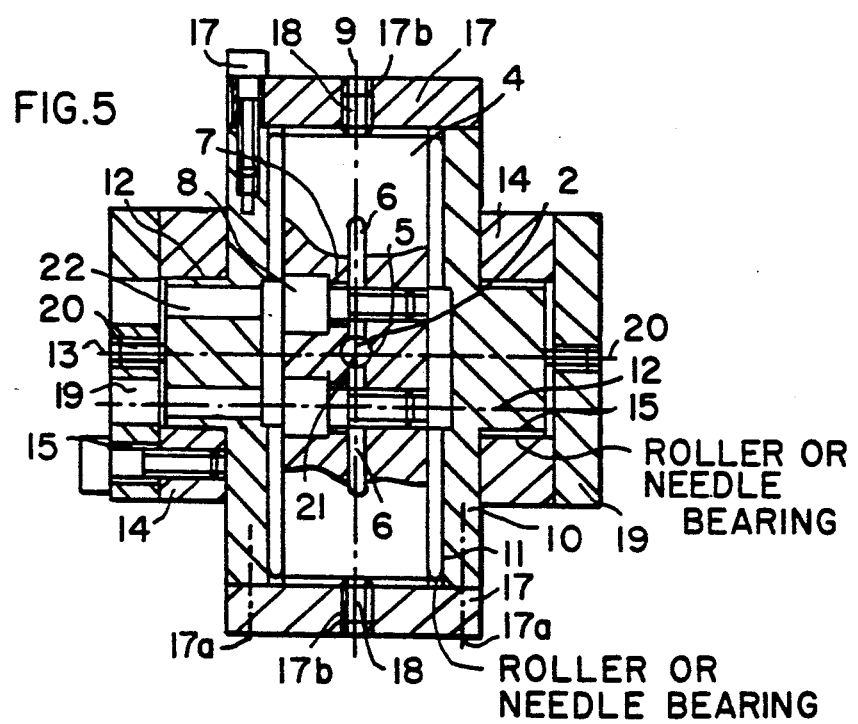

The embodiment shown in FIGS. 4 and 5 is quite similar to that of FIGS. 1 and 2, whereby FIG. 5 is a sectional view along section line V—V in FIG. 4. All components which are the same in FIGS. 4 and 5 as in FIGS. 1 and 2 have the same reference numbers in these FIGS. 1, 2, 4, and 5. In FIGS. 4 and 5 the sleeve bearing provided in the bore 11 in FIGS. 1 and 2 for the clamping shaft 4, has been replaced by an antifriction bearing in the form of a needle or roller bearing. A roller or needle bearing is also provided in the bore 15 of the support back 14 for the journal pins 12, if desired. Otherwise, the construction and function of the embodiment of FIGS. 4 and 5 are the same as described above with reference to FIGS. 1 and 2.

Figure 6:
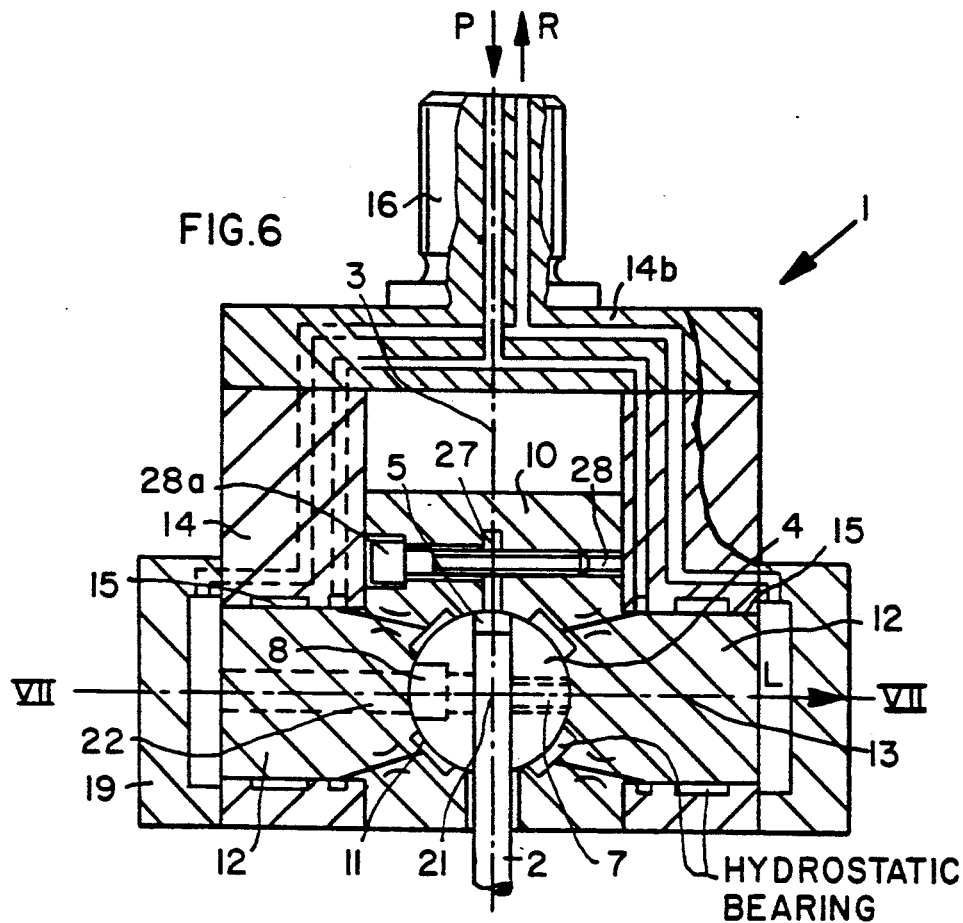
FIGS. 6 and 7 are views similar to FIGS. 1 and 3, but showing a hydrostatic bearing for the clamping shaft.
Figure 7:
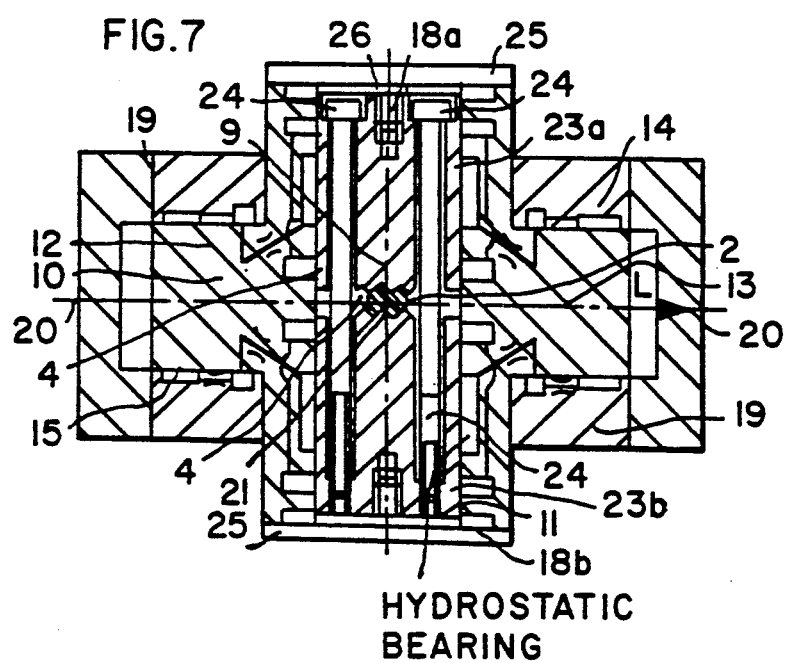

The embodiment shown in FIGS. 6 and 7 is quite similar to that of FIGS. 1 and 3, whereby FIG. 7 is a sectional view along section line VII—VII in FIG. 6. All components which are the same in FIGS. 6 and 7 as in FIGS. 1 and 3 have the same reference numbers in FIGS. 1, 3, 6 and 7. In FIGS. 6 and 7 the sleeve bearings provided in the bores 11 and 15 in FIGS. 1 and 3 have been replaced by respective hydrostatic bearings. Fluid conduits for the supply P and return R of hydraulic bearing fluid to the hydrostatic bearings are shown in FIGS. 6 and 7. Flow restrictions, such as throttling devices, are provided in the supply conduits for the bearing fluid. The supply P and return conduits R may pass through the threaded mounting member 16 as shown in FIG. 6. Otherwise, the embodiment of FIGS. 6 and 7 is constructed substantially as the embodiment of FIGS. 1 and 3 and the operation is also the same as described above with reference to FIGS. 1 and 3.

FIG. 7 also shows that the sample facing wall surfaces of the clamping shaft sections 23a, 23b comprise grooves and ridges therein for gripping the test sample 2 in a form-locking and force-locking manner.

Although the invention has been described with reference to specific example embodiments, it will be appreciated that it is intended to cover all modifications and equivalents within the scope of the appended claims.

What I claim is:

1. A clamping device having a central longitudinal loading axis (3), for holding a test sample (2) free of any bending moments, comprising a mounting buck (14) for connection to a testing machine, first journal bearing means (15) defining a first journalling axis (13) in said mounting buck (14), a support member (10) having journal pins (12) journalled in said first journal bearing means (15), a clamping shaft (4) including means for holding said test sample, said clamping shaft (4) having journalling means (18) for journalling said clamping shaft (4) in said support member (10), second journal bearing means forming bores (17b) in which said journalling means (18) of said clamping shaft (4) are received for journalling said clamping shaft (4) and to define a second journalling axis (9), said first journalling axis (13) and said second journalling axis (9) extending at a right angle relative to each other and at a right angle relative to said loading axis (3), wherein said first and second journalling axes (13, 9) and said loading axis (3) have a common intersection (21), said clamping shaft (4) comprising threaded bores and clamping screw means (8, 24) for tightening said holding means of said clamping shaft to hold said test sample.

2. The clamping device of claim 1, wherein said first journal bearing means of said mounting buck comprises respective bores in which said journal pins (12) of said support member (10) are supported for journalling.

3. The clamping device of claim 1, wherein said holding means of said clamping shaft comprises a slot (6) located in a central symmetrical plane of said clamping shaft and a radial through-bore (5) forming a clamping bore for holding said test sample in a force-locking manner, said clamping screws extending perpendicularly across said slot (6).

4. The clamping device of claim 1, wherein said clamping shaft comprises two sections (23a, 23b) dividing said clamping shaft in a plane perpendicularly to said second journal axis of said clamping shaft, and wherein said clamping screws (24) interconnect said shaft sections for clamping said test sample between said shaft sections.

5. The clamping device of claim 4, wherein said clamping shaft sections have sample holding surfaces facing each other, said sample holding surfaces having grooves and ridges therein for gripping said test sample in a form-locking and force-locking manner.

6. The clamping device of claim 1, wherein said clamping shaft comprises a slot (6) for holding said test sample, said slot having walls provided with grooves and ridges for gripping said test sample in a form-locking and in a force-locking manner.

7. The clamping device of claim 1, wherein said support member and said clamping shaft are journalled in hydrostatic bearings.

8. The clamping device of claim 1, wherein said support member and said clamping shaft are journalled in anti-friction bearings.

9. The clamping device of claim 1, wherein said clamping shaft has a through-bore (5) for holding said test sample, said through-bore having walls provided with grooves and ridges for gripping said test sample in a form-locking and force-locking manner.

* * * * *